United States Patent
Choi et al.

(10) Patent No.: US 11,434,191 B2
(45) Date of Patent: Sep. 6, 2022

(54) MMA PREPARATION METHOD WITH ISOBUTENE INCLUDING SATURATED HYDROCARBON

(71) Applicant: HANWHA TOTAL PETROCHEMICAL CO., LTD., Seosan-Si (KR)

(72) Inventors: Hyun Chul Choi, Yongin-si (KR); Ho Sik Chang, Daejeon (KR); Jin Suk Lee, Seoul (KR); Yo Han Choi, Chungcheongnam-do (KR)

(73) Assignee: Hanwha Total Petrochemical Co., Ltd., Seosan-Si (KR)

( * ) Notice: Subject to any disclaimer, the term of this patent is extended or adjusted under 35 U.S.C. 154(b) by 0 days.

(21) Appl. No.: 17/076,292

(22) Filed: Oct. 21, 2020

(65) Prior Publication Data
US 2021/0139407 A1 May 13, 2021

(30) Foreign Application Priority Data
Nov. 13, 2019 (KR) .................. 10-2019-0145298

(51) Int. Cl.
*C07C 67/42* (2006.01)
*B01J 21/04* (2006.01)
(Continued)

(52) U.S. Cl.
CPC ............. *C07C 67/42* (2013.01); *B01J 21/04* (2013.01); *B01J 23/44* (2013.01); *C07C 69/54* (2013.01)

(58) Field of Classification Search
CPC ......... C07C 69/54; C07C 45/28; C07C 67/08; C07C 7/08; C07C 11/09; C07C 47/22;
(Continued)

(56) References Cited

U.S. PATENT DOCUMENTS 3,282,995 A * 11/1966 Whim .................... B01J 23/002
562/547
3,387,038 A * 6/1968 Koch ...................... C07C 47/22
568/477
(Continued)

FOREIGN PATENT DOCUMENTS

EP 0486291 A1 * 5/1992 ........... C07C 51/252
KR 20180047941 * 5/2018

OTHER PUBLICATIONS

KR20180047941 translation (Year: 2018).*

*Primary Examiner* — Yevgeny Valenrod
*Assistant Examiner* — Blaine G Doletski
(74) *Attorney, Agent, or Firm* — Harness, Dickey & Pierce, P.L.C.

(57) ABSTRACT

Disclosed is a method for preparing methyl methacrylate (MMA), the method including: (1) separating isobutene containing saturated hydrocarbon (n-butane and iso-butane), via a catalytic distillation process from a stream of $C_4$ hydrocarbons containing butadiene, n-butene, and isobutene; (2) producing methacrolein via a first oxidation reaction of the separated isobutene; (3) producing methacrylic acid via a second oxidation reaction of the produced methacrolein; and (4) esterifying the produced methacrylic acid with methanol. By having a high heat capacity, the amount of nitrogen added is minimized to reduce the size of the reactor and the amount of gas production at a rear end, which has a high economic feasibility due to the effect of reducing investment and investment cost.

5 Claims, 1 Drawing Sheet

Figure 1:
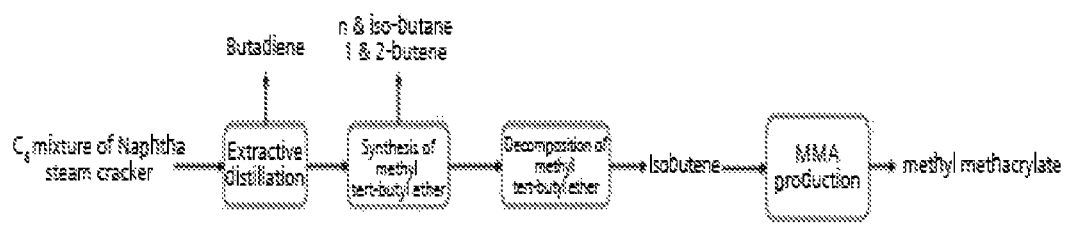

(51) Int. Cl.
*B01J 23/44* (2006.01)
*C07C 69/54* (2006.01)

(58) Field of Classification Search
CPC ....... C07C 51/252; C07C 57/04; C07C 67/42; C07C 51/16; B01J 21/04; B01J 23/44; Y02P 20/10; C10M 2205/0225; C10M 2207/1285; C10M 2205/0245; C10M 169/02; C10M 2205/0285; C10M 2207/026; C10N 2010/02; C10N 2020/02; C10N 2020/04; C10N 2030/02; C10N 2030/10; C10N 2040/02; C10N 2040/04; C10N 2050/10; C08F 4/6592
See application file for complete search history.

(56) References Cited

U.S. PATENT DOCUMENTS

| | | | | |
|---|---|---|---|---|
| 4,217,309 | A * | 8/1980 | Umemura | B01J 23/8877 502/308 |
| 5,144,091 | A * | 9/1992 | Martan | B01J 23/002 568/470 |
| 5,155,262 | A * | 10/1992 | Etzkorn | C07C 45/35 562/534 |
| 6,242,661 | B1 * | 6/2001 | Podrebarac | C07C 7/163 585/664 |
| 6,380,427 | B1 * | 4/2002 | Miyazaki | C07C 51/43 562/600 |

* cited by examiner

MMA PREPARATION METHOD WITH ISOBUTENE INCLUDING SATURATED HYDROCARBON

CROSS-REFERENCE TO RELATED APPLICATION

This application claims the benefit and priority of Korean Patent Application No. 10-2019-0145298 filed Nov. 13, 2019. The entire disclosure of the above application is incorporated herein by reference.

FIELD

The present disclosure relates to a method for preparing methyl methacrylate (MMA) using isobutene. More specifically, the present disclosure relates to a preparation method of methyl methacrylate (MMA), including oxidizing isobutene to obtain methacrolein, oxidizing methacrolein to obtain methacrylic acid, and esterifying methacrylic acid with methanol.

BACKGROUND

This section provides background information related to the present disclosure which is not necessarily prior art.

Isobutene used in preparation of methyl methacrylate is contained in $C_4$ hydrocarbon with butadiene collected from gas produced from cracking of petroleum. Thus, after separating the butadiene from the $C_4$ hydrocarbon, selectively reacting isobutene with methanol or water produces methyl tert-butyl ether (MTBE) or tert-butanol (TBA). Then, the MTBE or TBA is decomposed to obtain high-purity isobutene.

Further, as a catalytic distillation process that converts butadiene from a stream in a mixed $C_4$ hydrocarbon containing butadiene, n-butene and isobutene to n-butene and isomerizes butene-1 to butene-2 having a significantly different boiling point from that of isobutene for separation, in a distillation column reactor containing a palladium oxide catalyst therein, butadiene is converted to butene and most (>95%) of butene-1 is isomerized to butene-2, and isobutene, iso-butane and normal-butane are collected from a top of the distillation column reactor.

Further, in a method of isomerizing 1-butene as a reaction inhibitor in a $C_4$ olefin mixture to 2-butene to lower a concentration thereof, the $C_4$ olefin mixture is overhead distillate of a general reactive distillation process. In lowering the 1-butene content by passing the $C_4$ olefin mixture through a $Pd/Al_2O_3$ selective hydrogenation catalyst and by isomerizing 1-butene to 2-butene, the selective hydrogenation reaction is carried out under a mixed condition of gas phase and liquid phase.

The preparation method of methyl methacrylate (MMA) as an industrialized preparation process may include an ACH method using acetone as a starting material, a $C_4$ direct oxidation method in which methacrylic acid (MAA) is produced in a two-stage oxidation reaction using isobutene or tert-butyl alcohol (TBA) as a raw material, then the MAA is subjected to esterification to prepare the MMA, a MAN (methacrylonitrile) method in which isobutene (actually TBA) is used as a raw material and MMA is produced via methacrylonitrile, and the like.

Among the various techniques, isobutene as a starting material is contained in $C_4$ hydrocarbon of ethylene plant (NCC) or decomposed gasoline plant (FCC), and a technique for separating the isobutene therefrom is being developed simultaneously with the MMA process, in the $C_4$ direct oxidation method. Since isobutene and 1-butene in the $C_4$ hydrocarbons have approximate boiling points, it is difficult to separate them from each other via distillation. Thus, a reaction separation process using catalytic technology is being developed. In particular, Sumitomo Chemical is obtaining isobutene via methyl tert-butyl ether (MTBE). As an MTBE decomposition catalyst, a solid catalyst having a high selectivity and a long life as obtained by impregnating a metal sulfate into silica which in turn is subject to heat treatment has been developed and put into practical use.

After industrialization of the direct oxidation method, a demand of the MTBE as a gasoline additive has rapidly increased, because MTBE is present in large quantities as a product, thus making it easy to obtain the MTBE as a raw material for the direct oxidation method from anywhere in the world. Conversely, as the price of the MTBE is linked to the price of expensive gasoline, it is rather difficult to obtain the MTBE as an MMA raw material. That is why the $C_4$ direct oxidation method is not widely used.

However, environmental pollution due to storage of gasoline into underground tanks leads to reduction in demand of MTBE, and then the MTBE has become a global state of overcapacity. Thus, it is easy for companies that operate a decomposition process of MTBE for use to obtain the MTBE.

A core technology of the direct oxidation method is a two-step catalytic oxidation reaction. This reaction is the same type of reaction as synthesis of acrylic acid via a direct oxidation method of propylene. A first step catalyst is a Mo—Bi-based multi-components composite catalyst oxide similar to that for propylene oxidation. A second step catalyst is a P—Mo-based heteropoly acid catalyst having a structure different from that of Mo—V-based catalyst for oxidation of acrolein.

However, in the first step, isobutene has a different reactivity from that of propylene. When the catalyst for propylene oxidation is used as it is, activity thereof is too excessive, resulting in a low yield even when complete oxidation proceeds. In the second step, the P—Mo-based heteropoly acid itself does not exhibit a good yield. Further, a catalyst life thereof is shortened due to poor thermal stability thereof.

PRIOR ART LITERATURE

Patent Documents (Patent Document 0001) Korean Patent Application Publication No. 2002-0029083 (2002.4.17.)
(Patent Document 0002) Korean Patent Application Publication No. 10-2018-0047941 (2018.5.10.)

Non-Patent Documents (Non-patent document 0001) Sumitomo Chemicals, vol. 2004-II. p 4-14, Trends and Prospects of MMA Monomer Preparation Technology

SUMMARY

This section provides a general summary of the disclosure, and is not a comprehensive disclosure of its full scope or all of its features.

A purpose of the present disclosure is to solve the problems of the prior arts as described above. A purpose of the present disclosure is to provide a novel methyl methacrylate preparation process using a source containing isobutene with containing saturated hydrocarbon (n, and iso butane). 1-butene of a C4 olefin conversion plant is isomerized to convert to 2-butene, and at the same time, high concentration isobutene in a top of a reactive distillation column (CD-DelB overhead) is used, such that MMA is prepared without additional isobutene purification step, in an olefin conversion process.

In a general MMA preparation process, in order to obtain high-purity isobutene (isobutene 98% or greater) used as a raw material, a $C_4$ mixture containing isobutene is reacted with methanol or water to prepare MTBE or TBA, and then MTBE or TBA is separated from the $C_4$ mixture, and then high-purity isobutene is prepared via catalytic decomposition. Then, the isobutene is used in the MMA preparation process.

However, the present disclosure is to provide a process for preparing MMA in which 1-butene contained in the $C_4$ mixture is isomerized and converted into 2-butene having a high boiling point via a reactive distillation method, and an isobutene concentration in the $C_4$ mixture is 50 to 95%, and a concentration of isobutene in olefin excluding iso-butane and normal-butane contained in the $C_4$ mixture is 98% or greater, and thus, the $C_4$ mixture having the above-defined isobutene concentration therein is used for preparation of MMA, and the two steps of MTBE preparation and decomposition reaction in the prior art are reduced to one step reactive distillation.

The present disclosure for achieving the purposes provides a method for preparing methyl methacrylate in which an isobutene concentration of 50 to 95% in the $C_4$ mixture is used in consideration of economic efficiency while high-purity isobutene (98% or more) is used in the methyl methacrylate preparation process in the prior art, and the $C_4$ mixture in which the concentration of isobutene in olefin (isobutene, 1-butene, 2-butene) contained in the $C_4$ mixture is 98% or more is used.

The present disclosure for achieving the purposes provides a method for preparing methyl methacrylate, the method including extraction and reactive distillation to increase the concentration of the isobutene contained in the $C_4$ olefin, and oxidation and esterification of the isobutene contained in the product of the reactive distillation.

The present disclosure for achieving the purposes provides a method for preparing methyl methacrylate (MMA), the method including: (1) concentrating isobutene and saturated hydrocarbon (n-butane, iso-butane) a catalytic distillation process including an extractive distillation step of removing butadiene from a stream of C4 hydrocarbons containing butadiene, n-butene, isobutene, n-butane, and iso-butane as a feedstock and a reactive distillation step of removing n-butene containing 1-butene and 2-butene; (2) producing methacrolein by a primary oxidation reaction of the concentrate; (3) producing methacrylic acid via a secondary oxidation reaction of the produced methacrolein; and (4) esterifying the produced methacrylic acid with methanol.

(1) Step: $C_4$ hydrocarbon→isobutene
(2) Step: isobutene+$O_2$→methacrolein
(3) Step: methacrolein+$O_2$→methacrylic acid
(4) Step: methacrylic acid+methanol→methyl methacrylate (MMA)

A step of removing light gas may be included between the first oxidation reaction (isobutene→methacrolein) and the second oxidation reaction (methacrolein→methacrylic acid).

The light gas is a compound having a lower boiling point than that of the methacrolein, and includes CO, $CO_2$, $N_2$, and $O_2$.

The preparation method of methyl methacrylate of the present disclosure as described above, may obtain high-purity isobutene by a reactive distillation step. And the method, by using the isobutene containing saturated hydrocarbons of n-butane and iso-butane, may achieve the same level of control effect on reaction heat during the oxidation reaction of isobutene at a smaller amount of nitrogen added to control a maximum temperature of radical rapid reaction heat 450° C. below, due to the saturated hydrocarbon having a higher heat capacity than that of nitrogen without affecting the reaction itself. Compared to a conventional method in which the MTBE or TBA synthesis, and the MTBE or TBA decomposition, that is, the two steps are required, and excess nitrogen has to be added in the prior art, the present disclosure has the effect of reducing the process and thereby becoming highly economically feasible by minimizing the amount of the added nitrogen to reduce a reactor size and by reducing the amount of gas production at a rear end.

Further aspects and areas of applicability will become apparent from the description provided herein. It should be understood that various aspects of this disclosure may be implemented individually or in combination with one or more other aspects. It should also be understood that the description and specific examples herein are intended for purposes of illustration only and are not intended to limit the scope of the present disclosure.

BRIEF DESCRIPTIONS OF DRAWINGS

The drawings described herein are for illustrative purposes only of selected embodiments and not all possible implementations, and are not intended to limit the scope of the present disclosure.

Figure 2:
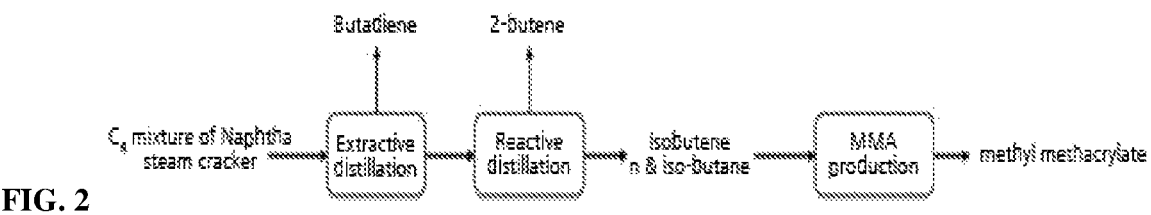

FIG. 1 is a flow diagram of an embodiment of the prior art.
FIG. 2 is a flow diagram of a preferred embodiment of the present disclosure.

DETAILED DESCRIPTION

Example embodiments will now be described more fully with reference to the accompanying drawings.

The present disclosure will be described in more detail. The present disclosure relates to a novel MMA preparation process using isobutene containing saturated hydrocarbon (n & iso-butane) in which MMA may be prepared without an additional isobutene purification process by utilizing isobutene at a top of the reactive distillation column (CD-DelB overhead) of an olefin conversion process.

The MMA preparation process of the present disclosure includes reactive distillation to increase isobutene concentration and MMA preparation process (isobutene oxidation reaction, and esterification reaction).

The MMA preparation process of the present disclosure includes a butadiene extraction distillation step in which butadiene is removed from a $C_4$ mixture of NCC containing butadiene, 1-butene, 2-butene, isobutene, n-butane and iso-butane, and a trace amount of $C_3$ gas; and, subsequently, a reactive distillation step of converting 1-butene to 2-butene and removing 2-butene using a boiling point difference. In this connection, 1-butene is completely converted to 2-butene, and 2-butene having a high boiling point is removed from a bottom of the reactive distillation column, such that a mixture containing isobutene, iso-butane and n-butane is produced.

Further, the MMA preparation process of the present disclosure may further include a step of removing light gas between the first oxidation reaction (isobutene→methacrolein) and the second oxidation reaction (methacrolein→methacrylic acid).

In one implementation, Pd/alumina catalyst is used as a catalyst for the reactive distillation process to increase the isobutene concentration in the $C_4$ olefin. An MMA preparation process catalyst employs an oxide catalyst in the first step, an oxide catalyst in the second step, and an ion exchange resin in the third step.

Hereinafter, the present disclosure will be described in more detail based on examples, but the present disclosure is not limited to the examples.

Preparation Example 1

The first oxidation reaction (isobutene methacrolein) was performed using only high-purity isobutene (99% or greater) as a raw material. A composition of reactants as added during the reaction is shown in Table 1 below.

TABLE 1

| Composition of reactants (molar ratio) | | | |
| --- | --- | --- | --- |
| Isobutene | Oxygen | Water | Nitrogen |
| 1 | 2.0 | 1.6 | 11.9 |

Preparation Example 2

A stream of $C_4$ hydrocarbon containing butadiene, n-butene and isobutene was used as a raw material. Isomerization of 1-butene contained in the $C_4$ hydrocarbon into 2-butene was carried out using a catalyst. Then, the 2-butene was removed from the bottom of the distillation column. A rest of the distillation column contained an isobutene-rich stream containing saturated hydrocarbon. The stream of the isobutene-rich saturated hydrocarbons was subjected to the first oxidation reaction (isobutene methacrolein) such that the isobutene was converted to methacrolein. The composition of the reactants injected during the reaction is shown in Table 2 below.

TABLE 2

| Composition of reactants (molar ratio) | | | | |
| --- | --- | --- | --- | --- |
| Isobutene | Isobutane | Oxygen | Water | Nitrogen |
| 1 | 0.266 | 2.0 | 1.6 | 11.63 |

Preparation Example 3

As in the preparation example 2, the isobutene-rich stream containing saturated hydrocarbon was separated from the raw material stream. The isobutene contained in the stream was subjected to the first oxidation reaction (isobutene methacrolein) such that the isobutene was converted to methacrolein. Table 3 shows the composition of the reactants injected during the reaction.

TABLE 3

| Composition of reactants (molar ratio) | | | | |
| --- | --- | --- | --- | --- |
| Isobutene | Isobutane | Oxygen | Water | Nitrogen |
| 1 | 0.266 | 2.2 | 1.6 | 11.43 |

A conversion rate of isobutene, and methacrylic acid selectivity and yield as shown in Examples and Comparative Example are calculated as follows:

Conversion rate of isobutene (mol %)=[added isobutene (mol)−isobutene after reaction (mol)]/added isobutene (mol)×100

Methacrylic acid selectivity (mol %)=produced methacrylic acid (mol)/[added isobutene (mol)−isobutene after reaction (mol)]×100

Methacrylic acid yield (mol %)=produced methacrylic acid (mol)/added isobutene (mol)×100

Comparative Example

According to the method of the present disclosure, isobutene oxidation was carried out while using the Preparation Example 1 as a feed. A reaction condition is shown in Table 4 below.

TABLE 4

| | First reaction (Isobutene → methacrolein) | Second reaction (methacrolein → methacrylic acid) |
| --- | --- | --- |
| Reaction temperature | 340° C. | 280° C. |
| Reaction pressure | 0.5 barg | 0.3 barg |
| Space velocity | 1,000 $h^{-1}$ | 800 $h^{-1}$ |
| Catalyst amount | 40 ml | 75 ml |

The isobutene conversion rate obtained under the above oxidation reaction conditions was 99.0 mol %, the methacrylic acid selectivity obtained under the above oxidation reaction conditions was 86.0 mol %, and the methacrylic acid yield obtained under the above oxidation reaction conditions was 56.0 mol %.

Example 1

According to the method of the present disclosure, an isobutene oxidation reaction was performed while using the Preparation Example 2 as a feed. The isobutene conversion rate and the methacrylic acid selectivity and yield as obtained via an oxidation reaction under the same reaction conditions as those of the Comparative Example are as follows.

The isobutene conversion rate was 99.0 mol %, the methacrylic acid selectivity was 87.0 mol %, and the methacrylic acid yield was 57.0 mol %.

Example 2

According to the method of the present disclosure, an isobutene oxidation reaction was performed while using the Preparation Example 3 as a feed. The isobutene conversion rate and the methacrylic acid selectivity and yield as obtained via an oxidation reaction under the same reaction conditions as those of the Comparative Example are as follows.

The isobutene conversion rate was 99.5 mol %, the methacrylic acid selectivity was 87.0 mol %, and the methacrylic acid yield was 57.5 mol %.

As described above, when the isobutene containing the saturated hydrocarbon is used as the raw material, the methacrylic acid selectivity and yield may be improved too.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A method for preparing methyl methacrylate (MMA), the method comprising:
   (1) concentrating isobutene comprising n-butane and iso-butane by a catalytic distillation process including an extractive distillation step of removing butadiene and a reactive distillation step of removing n-butene from a feedstock, wherein the feedstock is a stream of $C_4$ hydrocarbons containing butadiene, n-butene, isobutene, n-butane, and iso-butane;
   (2) removing light gas, between a first oxidation reaction and a second oxidation reaction;
   (3) producing methacrolein by the first oxidation reaction of the concentrated isobutene;
   (4) producing methacrylic acid via the secondary oxidation reaction of the produced methacrolein; and
   (5) esterifying the produced methacrylic acid with methanol.

2. The method of claim 1, wherein a catalyst in the catalytic distillation process is a Pd/alumina catalyst.

3. The method of claim 1, wherein a catalyst for the first oxidation reaction is an oxide catalyst.

4. The method of claim 1, wherein a catalyst for the second oxidation reaction is an oxide catalyst.

5. The method of claim 1, wherein the light gas comprises CO, $CO_2 N_2$ and/or $O_2$.

* * * * *